(12) United States Patent
DeBoer et al.

(10) Patent No.: US 8,172,865 B2
(45) Date of Patent: May 8, 2012

(54) SELECTABLE STROKE CUTTER

(75) Inventors: Charles DeBoer, Pasadena, CA (US); Matthew McCormick, Forest Falls, CA (US); Prashant R. Bhadri, Pico Rivera, CA (US); Aaron Barnes, Washington, DC (US); Ralph Kerns, Laguna Niguel, CA (US); Mark S. Humayun, Glendale, CA (US)

(73) Assignee: Doheny Eye Institute, Los Angeles, CA (US)

( * ) Notice: Subject to any disclaimer, the term of this patent is extended or adjusted under 35 U.S.C. 154(b) by 770 days.

(21) Appl. No.: 12/240,101

(22) Filed: Sep. 29, 2008

(65) Prior Publication Data
US 2009/0088784 A1   Apr. 2, 2009

Related U.S. Application Data

(60) Provisional application No. 60/975,630, filed on Sep. 27, 2007.

(51) Int. Cl.
*A61B 17/32* (2006.01)

(52) U.S. Cl. ........................ 606/167; 623/2.11

(58) Field of Classification Search .............. 606/79, 606/168, 169, 167; 623/2.11
See application file for complete search history.

(56) References Cited

U.S. PATENT DOCUMENTS

| | | | |
|---|---|---|---|
| 3,732,858 A | 5/1973 | Banko | |
| 3,882,872 A | 5/1975 | Douvas et al. | |
| 3,937,222 A | 2/1976 | Banko | |
| 3,976,077 A | 8/1976 | Kerfoot, Jr. | |
| 3,990,453 A | 11/1976 | Douvas et al. | |
| 4,167,944 A | 9/1979 | Banko | |
| 4,368,734 A | 1/1983 | Banko | |
| 4,428,748 A | 1/1984 | Peyman et al. | |
| 4,530,356 A | 7/1985 | Helfgott et al. | |
| 4,598,710 A | 7/1986 | Kleinberg et al. | |
| 4,662,869 A | 5/1987 | Wright | |
| 4,757,814 A | 7/1988 | Wang et al. | |

(Continued)

FOREIGN PATENT DOCUMENTS

WO    WO9305718    4/1993

(Continued)

OTHER PUBLICATIONS

International Search Report and Written Opinion in PCT/US08/078087 Dated Apr. 6, 2009.

(Continued)

*Primary Examiner* — Victor Nguyen
(74) *Attorney, Agent, or Firm* — Knobbe, Martens, Olson & Bear, LLP

(57) ABSTRACT

Apparatus, systems, and devices are described that utilize an adjustable biological tissue cutting handpiece that is based on selectable settings. The biological tissue cutting handpiece includes a cutter tip that allows multiple duty cycles as well as multiple port configurations. For example, when working next to the retina, the port could be adjusted to be a smaller size, allowing delicate membrane dissection. When working near or in less sensitive tissue, e.g. the center of the eye, the port could be wide open. The port aperture size can be independent of cut speed, allowing a surgeon to work at high speed both next to the retina and away from the retina. High speeds have been shown to have increased tissue (e.g., vitreous) removal, e.g., in 25 and 23-gauge instruments. Duty cycle is not necessarily dependent on cut speed, allowing high cutter performance and varied flow characteristics.

19 Claims, 8 Drawing Sheets

U.S. PATENT DOCUMENTS

| | | | |
|---|---|---|---|
| 4,811,734 A | 3/1989 | McGurk-Burleson et al. | |
| 4,844,064 A | 7/1989 | Thimsen et al. | |
| 4,850,354 A | 7/1989 | McGurk-Burleson et al. | |
| 4,867,157 A | 9/1989 | McGurk-Burleson et al. | |
| 4,895,166 A | 1/1990 | Farr et al. | |
| 4,908,015 A | 3/1990 | Anis | |
| 4,909,249 A | 3/1990 | Akkas et al. | |
| 4,911,161 A | 3/1990 | Schechter | |
| 4,940,468 A | 7/1990 | Petillo | |
| 4,983,179 A | 1/1991 | Sjostrom | |
| 4,986,827 A | 1/1991 | Akkas et al. | |
| 5,047,008 A | 9/1991 | De Juan, Jr. et al. | |
| 5,084,052 A | 1/1992 | Jacobs | |
| 5,106,364 A | 4/1992 | Hayafuji et al. | |
| 5,112,339 A | 5/1992 | Zelman | |
| 5,139,504 A | 8/1992 | Zeiman | |
| 5,346,497 A | 9/1994 | Simon et al. | |
| 5,403,276 A | 4/1995 | Schechter et al. | |
| 5,423,844 A | 6/1995 | Miller | |
| 5,437,630 A | 8/1995 | Daniel et al. | |
| 5,464,389 A | 11/1995 | Stahl | |
| 5,492,528 A | 2/1996 | Anis | |
| 5,562,691 A | 10/1996 | Tano et al. | |
| 5,613,972 A | 3/1997 | Lee et al. | |
| 5,630,827 A | 5/1997 | Vijfvinkel | |
| 5,690,660 A | 11/1997 | Kauker et al. | |
| 5,722,945 A * | 3/1998 | Anis et al. | 604/22 |
| 5,730,718 A | 3/1998 | Anis et al. | |
| 5,746,713 A | 5/1998 | Hood et al. | |
| 5,792,167 A | 8/1998 | Kablik et al. | |
| 5,827,292 A | 10/1998 | Anis | |
| 5,843,111 A | 12/1998 | Vijfvinkel | |
| 5,911,699 A | 6/1999 | Anis et al. | |
| 6,007,513 A | 12/1999 | Anis et al. | |
| 6,007,556 A | 12/1999 | Kablik et al. | |
| 6,027,514 A | 2/2000 | Stine et al. | |
| 6,203,518 B1 | 3/2001 | Anis et al. | |
| 6,217,543 B1 | 4/2001 | Anis et al. | |
| 6,258,111 B1 | 7/2001 | Ross et al. | |
| 6,342,061 B1 | 1/2002 | Kauker et al. | |
| 6,352,519 B1 | 3/2002 | Anis et al. | |
| 6,488,695 B1 | 12/2002 | Hickingbotham | |
| 6,514,268 B2 | 2/2003 | Finlay et al. | |
| 6,540,695 B1 | 4/2003 | Burbank et al. | |
| 6,629,986 B1 | 10/2003 | Ross et al. | |
| 6,638,235 B2 | 10/2003 | Miller et al. | |
| 6,730,106 B2 | 5/2004 | Kanda et al. | |
| 6,773,445 B2 | 8/2004 | Finlay et al. | |
| 7,013,566 B1 | 3/2006 | Bellm et al. | |
| 7,083,608 B2 | 8/2006 | Tomita et al. | |
| 7,276,032 B2 | 10/2007 | Hibner | |
| 7,470,277 B2 | 12/2008 | Finlay et al. | |
| 7,758,537 B1 | 7/2010 | Brunell et al. | |
| 2002/0052617 A1 | 5/2002 | Anis et al. | |
| 2004/0049217 A1 | 3/2004 | Ross et al. | |
| 2005/0256512 A1 | 11/2005 | Del Rio et al. | |
| 2006/0036270 A1 | 2/2006 | Terao | |
| 2006/0281599 A1 | 12/2006 | Murakami et al. | |
| 2007/0088376 A1 | 4/2007 | Zacharias | |
| 2007/0129732 A1 | 6/2007 | Zacharias | |
| 2007/0185512 A1 | 8/2007 | Kirchhevel | |
| 2007/0185514 A1 | 8/2007 | Kirchhevel | |
| 2007/0191758 A1 | 8/2007 | Hunter et al. | |
| 2008/0146965 A1 | 6/2008 | Privitera et al. | |
| 2008/0149197 A1 | 6/2008 | Turner et al. | |
| 2008/0172078 A1 | 7/2008 | Svetic | |
| 2008/0188881 A1 | 8/2008 | Chon | |
| 2009/0082715 A1 | 3/2009 | Charles | |
| 2009/0287233 A1 | 11/2009 | Huculak | |

FOREIGN PATENT DOCUMENTS

| | | |
|---|---|---|
| WO | WO2008029066 | 3/2008 |
| WO | WO2008080148 | 7/2008 |
| WO | WO2009042991 | 4/2009 |

OTHER PUBLICATIONS

International Search Report and Written Opinion in PCT/US2010/030296 Dated May 21, 2010.

Written Opinion in PCT/US07/088745 Dated Jul. 2, 2009.

Extended European Search Report dated May 24, 2011 in European Application No. 07865997.6, filed on Dec. 21, 2007.

International Preliminary Report on Patentability and Written Opinion dated Oct. 20, 2011 in PCT/US2010/030296, filed on Apr. 7, 2010.

International Search Report mailed on Jun. 2, 2008 in PCT/US2007/088745, filed on Dec. 21, 2007.

PCT International Preliminary Report on Patentability issued Jun. 24, 2009 in PCT/US2007/088745, filed on Dec. 21, 2007.

PCT International Preliminary Report on Patentability Issued on Mar. 30, 2010 in PCT/US2008/078087.

\* cited by examiner

FIG. 7

| | | |
|---|---|---|
| Thin Horizontal Slit<br>702A | 0.004" wide<br>0.0145" deep | ○ Membrane removal<br>○ Shaving vitreous base<br>○ Detached retina |
| Grater<br>702B | Tip perforated with 0.008" diameter holes | ○ Shaving the retina<br>○ Working close to detached retina<br>○ Possibly membrane removal |

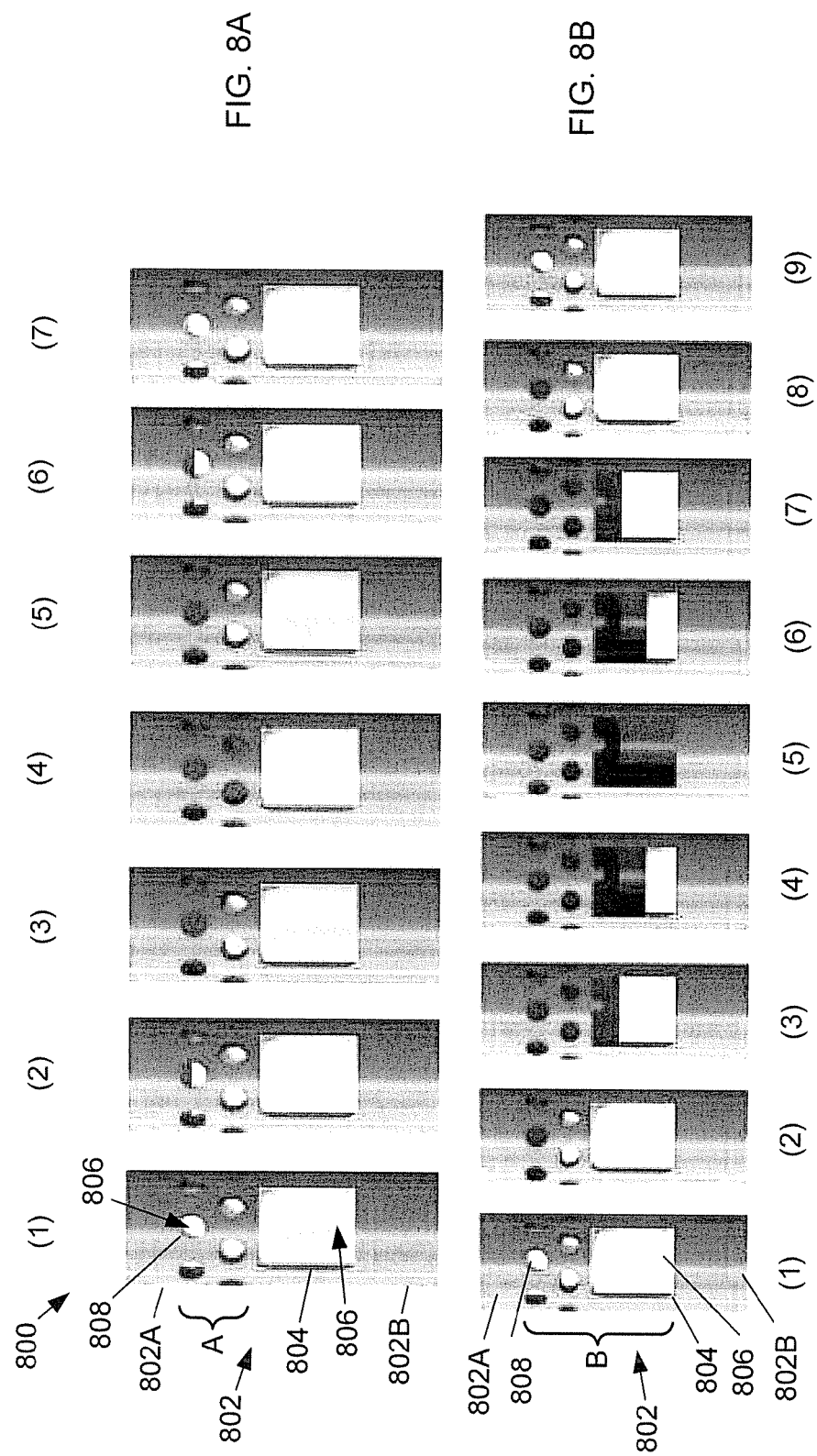

SELECTABLE STROKE CUTTER

RELATED APPLICATION

This application claims the benefit of U.S. Provisional Patent Application No. 60/975,630 filed 27 Sep. 2007, the entire content of which is incorporated herein by reference.

BACKGROUND

Prior art biological tissue cutting handpieces, e.g., as currently available on the market, are either pneumatic or electric. Both types of such biological tissue cutting handpieces have a single port and fixed size, and typically allow only one stroke length. Spring return pneumatic handpieces have a variable duty cycle, which is reduced as speed is increased. Dual line pneumatics handpieces currently operate at a constant duty cycle and do not have adjustable port apertures. Neither of these types of biological tissue cutting handpieces allows for a selectable stroke.

Some prior art techniques have endeavored to vary the size of the port aperture, but most of these prior art techniques have varied the port with cut speed. This is essentially an extension of prior art pneumatic drive techniques/apparatus, where the duty cycle (the percentage of time the port is open) reduces as cut speed increases leading to a point where the cutter is no longer allowed to completely open. Other prior art techniques address port configurations with manual adjustments.

While such prior art techniques may be suitable for their respective intended purposes, there exists a need for techniques that provide improved adjustability of handpiece performance characteristics.

SUMMARY

Embodiments of the present disclosure can provide techniques, e.g., apparatus and methods, that utilize a selectable stroke biological tissue cutting handpiece that is selectable based on machine settings. Each individual stroke can have a unique cut profile or linear trajectory of the cutting blade tip as it extends and retracts. The cut profile can be defined as the linear path of the cut. The linear path can include an acceleration profile, duty cycle, and can have the potential to use multiple strokes per rotation of the motor. To expand upon this, it is possible to have the cutter (or cutting blade tip) operate at one speed in one direction (with a unique stroke length and duty cycle), and operate at two times the speed in the opposite direction. This could be achieved with a double stroke cam. The biological tissue cutting handpiece can include a cutter tip or cutting blade tip that allows multiple duty cycles as well as multiple port configurations. For example, when working next to the retina, the port would be adjusted to be a smaller size, allowing precise tissue removal with the cutting blade tip. When working in the center of the eye, the port would be wide open. Exemplary embodiments can be used for vitrectomy procedures.

The cut profile and hence port aperture size are independent of cut speed, allowing a surgeon to work at high speed both next to the retina and away from the retina. High speeds have been shown to increase vitreous removal, e.g., in 25 and 23-gauge instruments. Furthermore, duty cycle is not dependent on cut speed, allowing high cutter performance and varied flow characteristics. When working away from the retina, the stroke length may be much larger than the port aperture. This can further increase flow because vitreous would enter the outer needle easier.

One difference between embodiments of the present disclosure e.g., instrument, and the prior art is that the drive mechanism as disclosed adjusts the stroke (and hence port configuration) automatically. One mechanism is by reversing the drive direction (e.g., from clockwise to counterclockwise). Exemplary embodiments can be applicable for a specific sinusoidal full modulation. By reversing the motor, the linear cut profile can be changed (including duty cycle, stroke length, acceleration, and any other specific for a cut profile).

In exemplary embodiments of the present disclosure, the cutter may also be used in a proportional handpiece mode, where the position of the cutter is moved in a precise method controlled by the surgeon. This may be used with specialized tips to allow membrane manipulation with the vitrectomy cutter tip (cutting blade tip). The vitrectomy cutter tip may replace the forceps for some procedures.

Other features and advantages of the present disclosure will be understood upon reading and understanding the detailed description of exemplary embodiments, described herein, in conjunction with reference to the drawings.

BRIEF DESCRIPTION OF DRAWINGS

Aspects of the disclosure may be more fully understood from the following description when read together with the accompanying drawings, which are to be regarded as illustrative in nature, and not as limiting. The drawings are not necessarily to scale, emphasis instead placed on the principles of the disclosure. In the drawings:

FIG. 7 is a table depicting two exemplary configurations of cutting tips and listing corresponding exemplary applications, according to the present disclosure; and FIG. 8 includes FIGS. 8A-8B, which show a cutter with cutting blade tip operating over different selectable stroke ranges, in accordance with an exemplary embodiment of the present disclosure.

Figure 1:
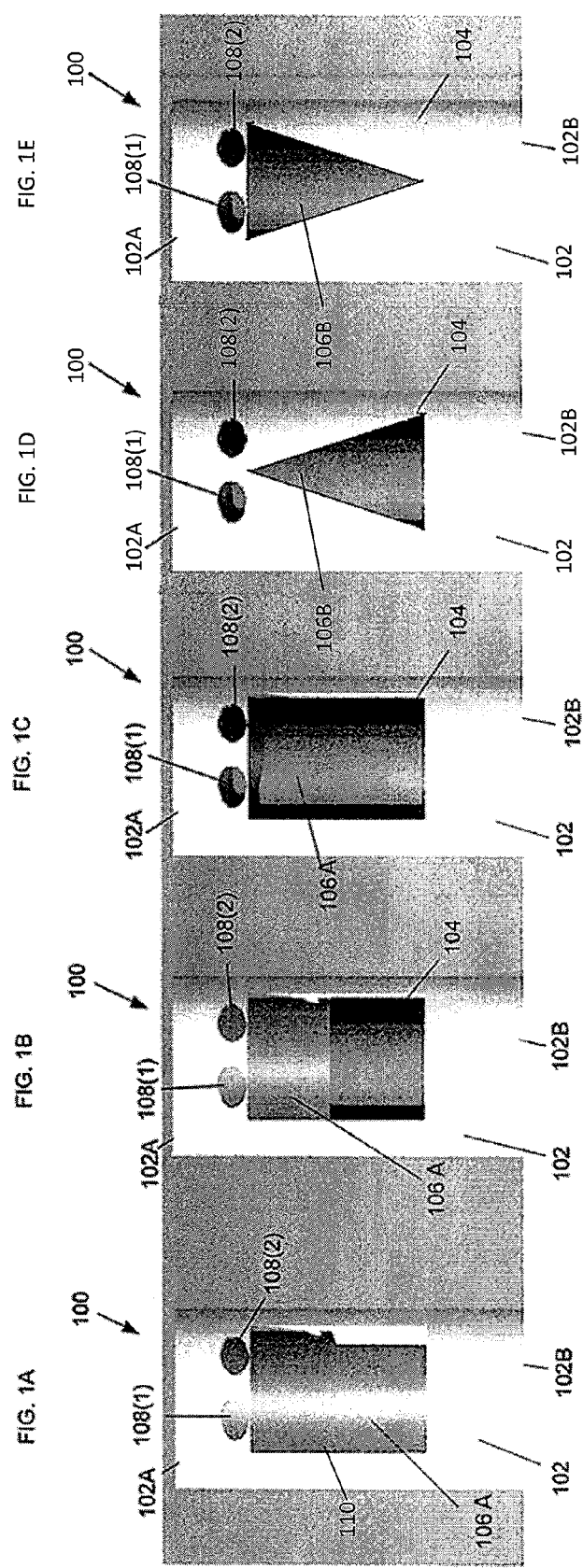
FIG. 1 includes FIGS. 1A-1E, which depict a biological tissue cutting tip and cutting blade tip (cutter) at various positions of operation and as configured and arranged for large stroke cutting, in accordance with exemplary embodiments of the present disclosure.

While certain embodiments depicted in the drawings, one skilled in the art will appreciate that the embodiments depicted are illustrative and that variations of those shown, as well as other embodiments described herein, may be envisioned and practiced within the scope of the present disclosure.

DETAILED DESCRIPTION

Aspects and embodiments of the present disclosure are directed to techniques, e.g., apparatus and methods, that utilize a selectable stroke biological tissue cutting handpiece. The biological tissue cutting handpiece can include a cutter tip that allows multiple duty cycles as well as multiple port configurations (size), and selectable stroke length.

Embodiments of the present disclosure are directed to devices/methods/apparatus that provide a selectable cut profile, which encompasses but is not limited to duty cycle, variable port size, and selectable stroke length cutter. These are independent of speed to allow full surgical control of the handpiece. The cut profile can also encompasses things like multiple strokes per revolution (e.g., by use of a speed doubler), various acceleration and deceleration paths, etc. Furthermore, innovative port configurations can be used to further optimize the cutter tip.

During vitreous surgery, a surgeon typically requires high flow rates (of tissue removal) when away from the retina and reduced flow rates for more controlled cutting when close to the retina. Furthermore, there is a need to use a biological tissue cutting handpiece to remove membranes that are close to the retina.

Embodiments of the present disclosure provide a device having a port that can be selected to accommodate these needs. Furthermore, embodiments of the present disclosure can provide a duty cycle that can be used to maintain flow rate with small apertures as well as large apertures. Such can allow controlled flow throughout the cut range. For example, when working next to the retina, the port would be selected to be a smaller size, allowing delicate membrane dissection.

Embodiments of the present disclosure can provide a device, e.g., vitreous cutter tip 100 of FIG. 1, that can allow easily selectable port configuration. When working close to the retina, the device aperture can be reduced allowing more precise removal. When bulk vitreous removal is desired, the port would be wide open. This can be combined with multiple port configurations to allow a reduced port aperture mode that prevents the biological tissue cutter (e.g., vitrectomy device or vitrector) from cutting the retina. For example, the cutter could have a port configuration where one port has a rectangular shape distal from the end and second port with two semicircular openings proximal the end. When the cutter is partially closed, there are two small ports. The retina may have difficulty entering the two small ports. This can allow for delicate tissue removal next to the retina. Then, as the stroke is increased, the port can open further, crossing both ports, as shown in FIG. 1 thereby allowing increased vitreous removal. Exemplary embodiments of ports can include a port with a keyhole shape that has a narrow vertical section near the distal end of the tip and a wider end away from the tip, or a triangular shape.

Embodiments of the devices according to the present allows selectable duty cycle (which is one aspect/variable influencing the cut profile) independent of cut speed. Increasing flow due to more efficient high-speed cutting can be coupled with increased duty cycle for maximal removal rates. Small apertures (e.g., as shown in FIG. 1) can be combined with a large duty cycle to allow predictable flow through a narrow port. When working with a reduced aperture, cutters according to the present disclosure can also be run at any speed.

Furthermore, embodiments of the present disclosure can be operated with large duty cycles at high speeds as well as low speeds. This increased variability will allow the surgeon to vary flow either with port size or with speed. Currently spring return pneumatic cutter duty cycles are solely controlled with speed. This indicates that at high speed, reduced duty cycles account for lower flow rates. With small diameter instruments (23, and 25 gauge) the surgeon must use high vacuum levels. Typically 550 mmHg are used in the 25-gauge instrumentation. Then with a pneumatic cutter, the duty cycle is lowered, reducing flow.

Figures 2, 2A, 2B, 2C:
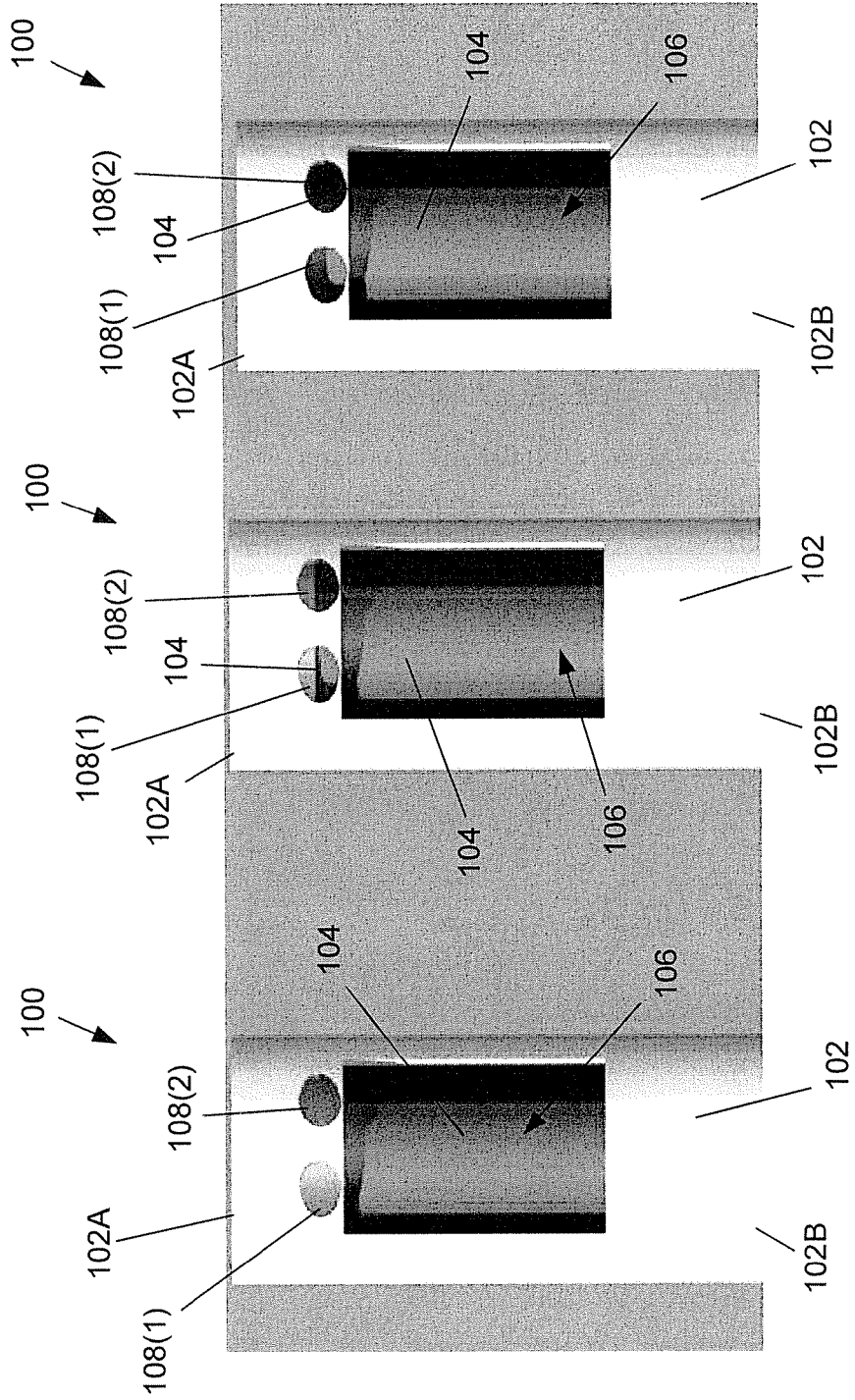
FIG. 2 includes FIGS. 2A-2C, which depict a biological tissue cutting tip and cutting blade tip similar to that of FIG. 1 as configured and arranged for smaller stroke cutting, according to an exemplary embodiment of the present disclosure.

Tip Design:

A cutting tip according to embodiments of the present disclosure can be configured to work close to delicate tissue, e.g., the retina. The port can be rectangular, allowing a size change capability, or it can have additional functionality. Furthermore, the tip design can have different characteristics as the stroke increases or decreases. Referring to FIGS. 1-2, an embodiment is shown that has minor ports that only cuts vitreous when there is a small stroke (the cutter crosses two small circular holes) and also a major port. When the stroke is larger, the operation port area extends into a rectangular port that allows high tissue (e.g., vitreous) removal rates.

FIG. 1 includes FIGS. 1A-1E, which depict a system 100 of a vitrectomy cutting tip 102 and cutter (cutting blade tip) 104 at various positions of operation, e.g., as configured and arranged for large stroke cutting, in accordance with an exemplary embodiment of the present disclosure.

The cutting tip 102 of system 100 includes distal end 102A and a proximal end 102B, a major port 106, and two minor ports 108(1)-108(2). In some embodiments, the major port is generally a deep groove 110. Certain embodiments include a rectangular port 106A, and other embodiments include a triangular port 106B. The cut profile of the ports, 106 and 108(1)-108(2) can be independent of cut speed, allowing a surgeon to work at high speed both next to the retina and away from the retina. High speed cutting of vitreous has been shown to have increased vitreous removal rate, e.g., in 25 and 23-gauge instruments. Furthermore, duty cycle is not necessarily dependent on cut speed, allowing improved performance and varied flow characteristics, as an increased duty cycle increases flow rate and vice versa. For example, when working away from delicate tissue, e.g., the retina, the stroke length may be much larger than the port aperture height of the minor ports 108(1)-108(2), for increased removal flow rate.

With continued reference to FIG. 1, larger stroke lengths, e.g., that extend beyond the distal end of the port major port (the end furthest away from the drive mechanism), can be implemented to further increase flow characteristics, e.g., volumetric flow rate. These strokes can be independent of cut speed allowing full control of tissue (e.g., vitreous) removal. The larger stroke can allow a lager volume chamber for the tissue to enter. This is so because the smaller inner diameter of the cutting blade tip in such a case will be further away from the port. Because of this, the tissue can enter the outer needle and flow further up the inner diameter of the outer tip.

FIG. 2 includes FIGS. 2A-2C, which depict a system 100 with a biological tissue cutting tip and cutter similar to that of FIG. 1 (with the same reference characters) as configured and arranged for smaller stroke cutting, according to an exemplary embodiment of the present disclosure. As shown in FIG. 2, the stroke of the cutter (or cutting blade tip) 104 during its reciprocating motion can be limited to the height (extent along the longitudinal direction) of the minor ports 108(1)-108(2), for which configuration flow would be decreased as the larger port 106 is not being opened.

Drive Design:

The cutting tips and devices herein can be used with suitable driving motors and mechanisms. Any of multiple drive technologies can accommodate these requirements. For example, voice coil technology may be used in exemplary embodiments. For such embodiments, the voice coil will move according to voltage and frequency supplied. It should allow long displacements and accurate positioning.

In general, any suitable type of electroactive element, may be used for driving a cutting tip blade in embodiments of the present disclosure. Such driving means/drive technologies can be used in conjunction with a lever arm to increase throw of the cutter (cutting blade tip). In exemplary embodiments, piezoelectric or electrorestrictive based drives can be used. Piezo drives can provide extremely accurate distance measurements. Other techniques of increasing piezo displacements can include (but are not restricted to) using dissimilar materials for flexing/bending a lever arm. In exemplary embodiments, suitable examples of these types of drives are manufactured by MIDE of 200 Boston Ave., Suite 1000, Medford, Mass. 02155, USA.

Pneumatic Drive mechanisms can be used in exemplary embodiments. Currently many pneumatic drives are spring driven and have variable duty cycle. For such embodiments, a pressure pulse can be used to push on a diaphragm and extend the cutting blade tip distally. The pressure pulse is then removed and a spring pushing the opposite direction causes the cutting blade tip to retract. The maximum pressure of the pulse is used to extend the instrument, and a pressure equal to the atmosphere is used during retraction of the cutting blade tip. If, instead the pressure is not released to atmospheric pressure, but some intermediate between the maximum pressure and atmospheric pressure, the cutting blade tip will not completely retract. This allows for it to have multiple cut profiles.

Other drive mechanisms are possible within the scope of the present disclosure. For example, it is contemplated that electroactive polymers could be used for driving a cutting tip blade. The embodiments of the present disclosure rely on the movement of the cutter tip and there are multiple ways to achieve such movement. One skilled in the are will appreciate that the present disclosure should not be limited by any particular type of drives, and further that the present disclosure and claimed devices/systems will have increased utility as new drive types are subsequently enabled.

Flow Control:

Flow will be controlled with both vacuum and cut profile. Because duty cycle does not reduce as speed increases, flow will not be reduced at increased speed. Conversely, the increased flow characteristics from rapid cutting can be coupled with a large stroke and large duty cycle to allow maximal removal rates. This is especially important in small diameter instruments (e.g., 23 and 25-gauge) where clogging effects can dominate the flow conditions.

Surgical Control:

The surgical interface, of exemplary embodiments, can be done with current dual linear foot pedals, e.g., as shown and described in U.S. Pat. No. 6,179,829, the entire contents of which are incorporated herein by reference, or with a controller that has basic settings. Of course, embodiments do not have to employ the use of a foot pedal for control, and may use other types of control, e.g., by the use of hand controls, or voice actuation, etc. These may be discrete settings (e.g., working for bulk removal, close to the retina, on the retina). These bulk settings can automatically adjust the stroke of the cutter, and the maximum aspiration pressure. Furthermore, the yaw component can be used to increase/decrease aspiration pressure from nominal. For example, when the pedal is in the top third of the travel bulk vitreous removal rates are used, in the middle third, the settings are reduced, and at the end of the travel retinal shaving settings are used.

Alternate modes of control include proportional motion of the inner cutter tip. This can be done for manipulating tissue (e.g., most likely no vacuum level). For instance, the surgeon can aspirate a membrane into the tip. Then the port can be mostly closed, just enough to clamp the tissue. Next the tissue can be manipulated. Furthermore, if the inner cutter tip or port were angled (e.g., so one side of the port closed before the other side), then there would be a natural clamping/gripping.

Figure 3:
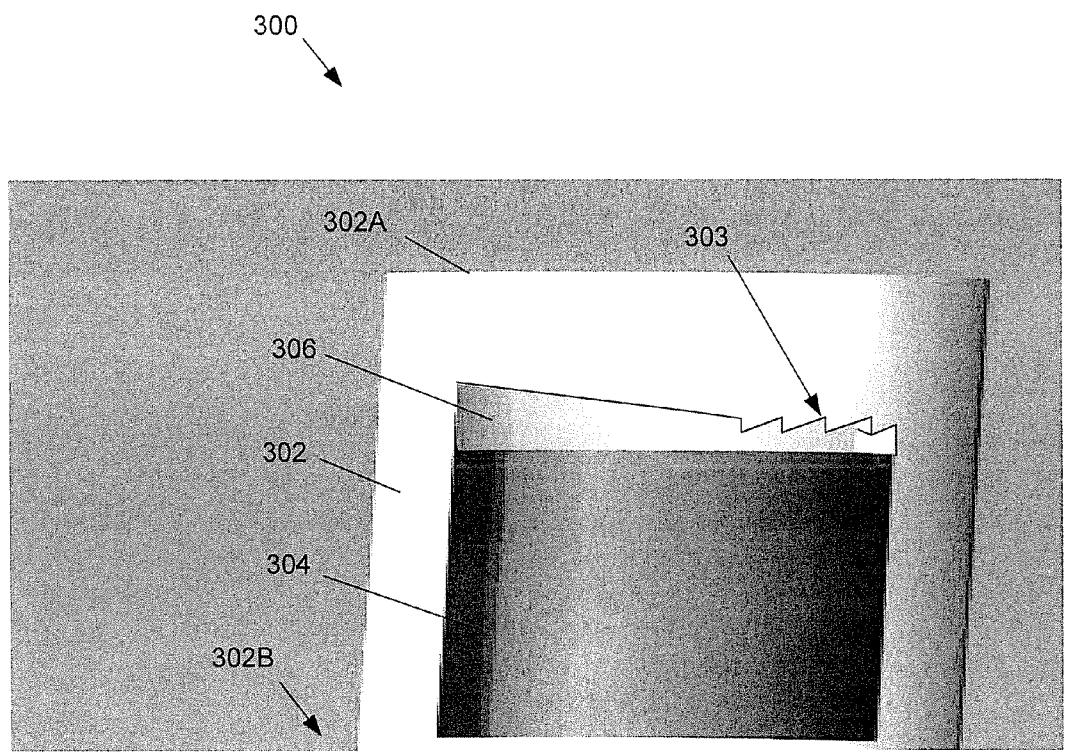
FIG. 3 depicts a biological tissue cutting tip with a gripping port configured with a manipulation section (saw-tooth configuration) for tissue manipulation, in accordance with a further embodiment of the subject disclosure.

Proportional Handpiece Operation:

FIG. 3 depicts a biological tissue cutter system 300 with a gripping port configured with a manipulation section (sawtooth configuration) for tissue manipulation, in accordance with a further embodiment of the subject disclosure. A shown, system 300 can include a cutting tip 302 that is configured and arranged to receive a cutting blade tip 304 that moves in a reciprocating motion. Cutting tip can include a proximal end (or portion) 302B and a distal end 302A. An aperture or port 306 can be disposed in cutting tip 302 and may be configured and shaped as desired. In the embodiment shown, port 306 is with a gripping port configured with a manipulation section (saw-tooth configuration) for tissue manipulation. Other port configurations may also or alternatively be used.

Figure 4:
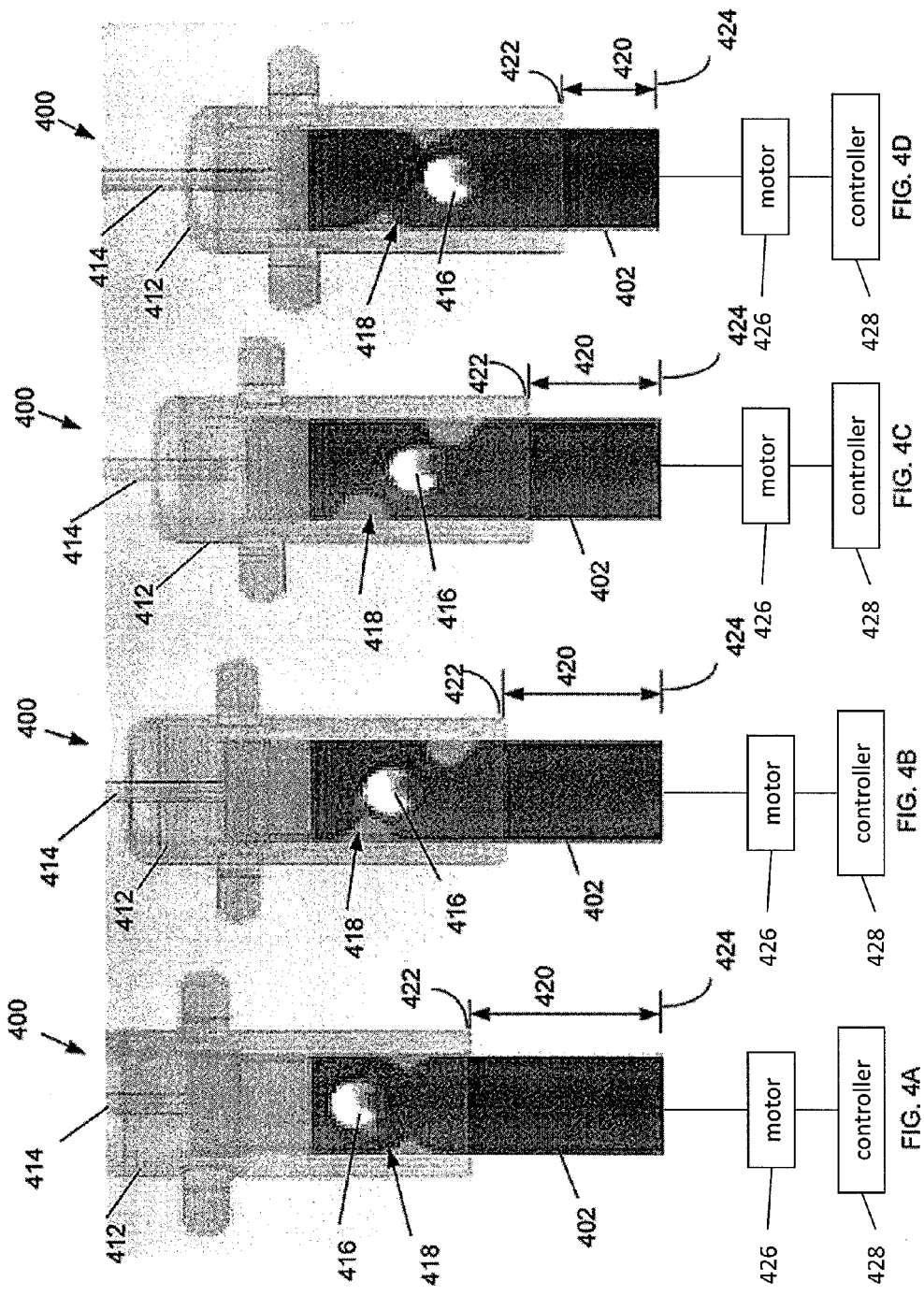
FIG. 4 includes FIGS. 4A-4D, which depict a cam mechanism and biological tissue cutting tip at different positions of operation.

FIG. 4 includes FIGS. 4A-4D, which depict a system 400 that includes a cam mechanism and biological tissue cutting blade as connected to a cutting tip (not shown) at different positions of operation. System 400 includes a rotary drive (e.g. drive shaft) 402, which can be driven by a suitable motor 426 controlled by a controller 428, and a driver housing 412 configured to receive the drive 402 and to hold a cutter blade 414. Cutter blade 414 is configured and arranged for use with a cutting tip, e.g., tip 302 as shown and described for FIG. 3.

With continued reference to FIG. 4, it can be seen that a ball 416 is held within driver housing 412, e.g., in a depression or scalloped or detent region, and is received by a groove 418 in rotating drive 402. Consequently, in operation of system 400, as drive 402 rotates, the angular motion of drive 402 is converted to reciprocating linear motion of cutter blade 414. This linear reciprocating motion can be seen in FIGS. 4A-4D by noticing the change in height 420, between a proximal end shown by reference line 422 (relative to cutter 414) of the driver housing 412 and a reference line 424. The groove 418 may be configured as appropriate, e.g., with a generally sinusoidal configuration, to provide a desired duty cycle for the cutting tip 414.

Figure 5:
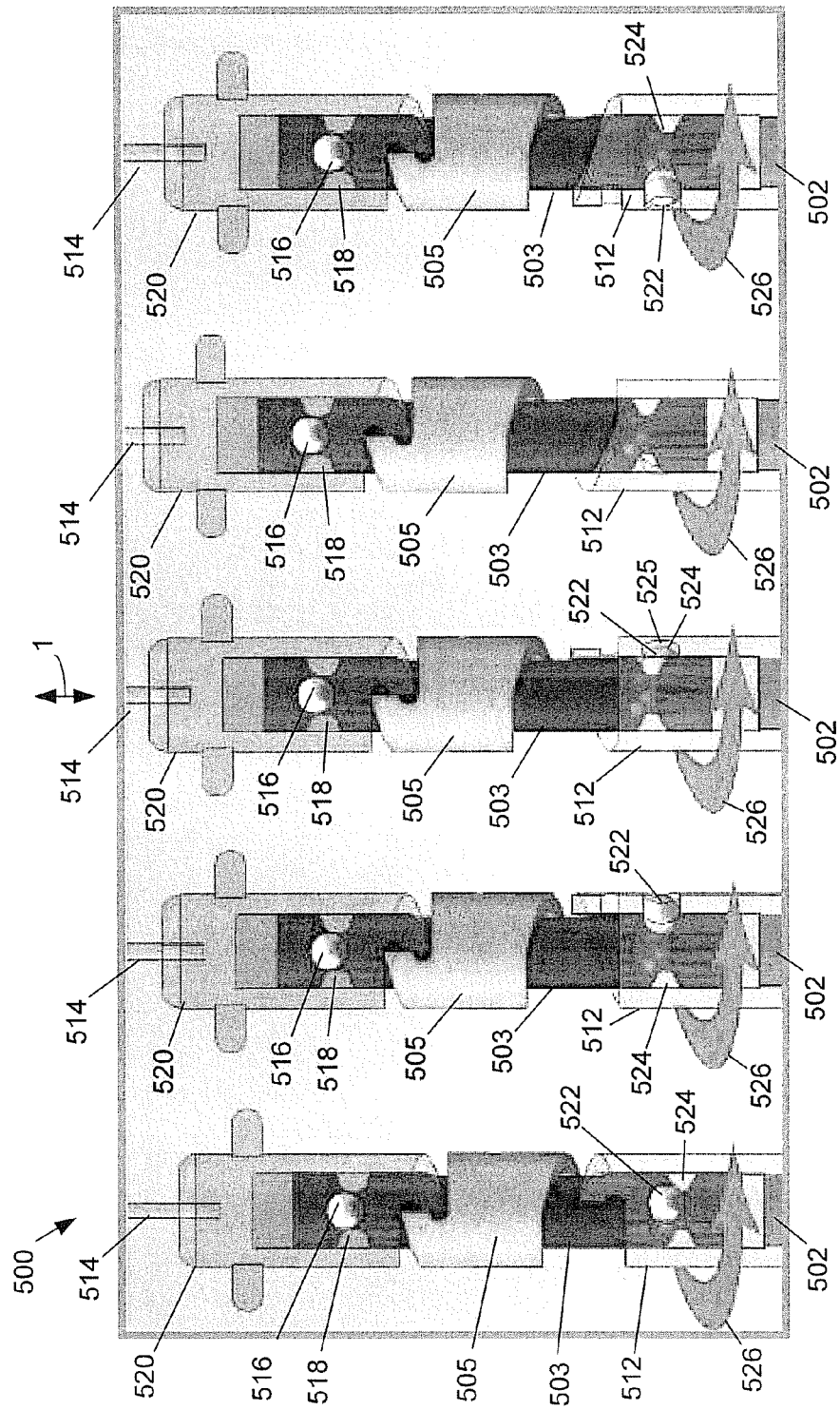
FIG. 5 includes FIGS. 5A-5E, which depict cams and locking mechanisms used during a cutting tip operation and shown in different positions of operation.

FIG. 5 includes FIGS. 5A-5E, which depict a system 500 with two drives (e.g., drive shafts), two cams, and locking mechanisms used with a cutting tip, in accordance with a further embodiment of the present disclosure. System 500 is shown in the figures in different positions of operation. System 500 is similar to system 400 of FIG. 4 with the addition of a two-drive mechanism (e.g., two drive shafts or drivers) including a first driver 502 and a second driver 503. System 500 also includes a locking mechanism (configured as a sleeve) 505, a first drive housing 512; and second drive housing 520. First driver 502 can be securely connected to first housing 512 and likewise second housing 520 can be securely connected to cutting tip 514.

As mentioned previously, system 500 includes two cams, which allow system 500 to operating with one of two different reciprocating motions. Similar to the embodiment of FIG. 4, the cams can each include a ball held by a sleeve of a drive housing and received by a groove of a driver (or drive shaft), e.g., shaft 503. As shown, the first drive housing includes a detent or cup shaped depression 525 for receiving and holding ball 522. Likewise, the second drive housing 520 includes a detent or cup shaped depression (not numbered) for receiving and holding ball 516. It should be understood that while two drives and cams (e.g., ball and groove systems) are shown, and practical desired number of such drives and cam may be utilized to provide more than two different and selectable reciprocating motions to cutter 514.

In operation, locking mechanism 505 slides along the drive 503 in the longitudinal direction. Locking mechanism may be moved by suitable means, e.g., manual adjustment by a user, pneumatic selection, solenoid actuation, etc. Referring to FIG. 5, by rotating the drive, 502 in the clockwise direction (as shown), the locking mechanism is pushed to the top portion (as shown), by 512, preventing rotation between 520 and 503. When the motor is rotated in the opposite direction, 505 is pushed down automatically by 520, causing it to lock with 512. This pushing motion occurs when the drive shaft moves in an opposite direction to the locking mechanism. Note that 505 is held in the same angular position as 503, so it never rotates relative to 503. In one direction, i.e., at one extreme of the longitudinal range as shown in FIG. 5, locking mechanism 505 prevents the second drive housing 520 from moving relative to the second drive 503. In this situation, the ball 522 (secured in detent 525) of the other cam travels in groove 524 as drive 502 rotates (based on motion from 502), consequently driving the cutter blade 514 in a reciprocating motion 1 controlled by the configuration of groove 524.

When located at the opposite direction at the other extreme of its longitudinal range (e.g., with the lower portion of 505 locked against drive 512), the locking mechanism 505 prevents the bottom drive 512 from moving relative to the second drive 503. In such a configuration, the ball 516 (held by associated detent) of the other (and now movable) second drive 520 causes the cutter blade 514 to move in a reciprocating motion (with a different cut profile than 1) that is controlled by the configuration of groove 518 in drive 503. Because of such a configuration, two reciprocating cut profiles (e.g., linear motions) (with controlled plunge depth and/or acceleration in the longitudinal direction) can be controlled by the rotation of the input drive 502 and the geometry of the respective grooves 524 and 518. The resulting linear motion produced by the selected cam and groove contribute with other factors (described supra) to the overall cut profile. While selection of a particular cam/profile can be operated manually, it is preferable to have this automatic, based on the direction the motor turns. Then the surgeon does not have to adjust anything by hand. Furthermore, this overcomes the limitations of previous manual designs.

Figure 6:
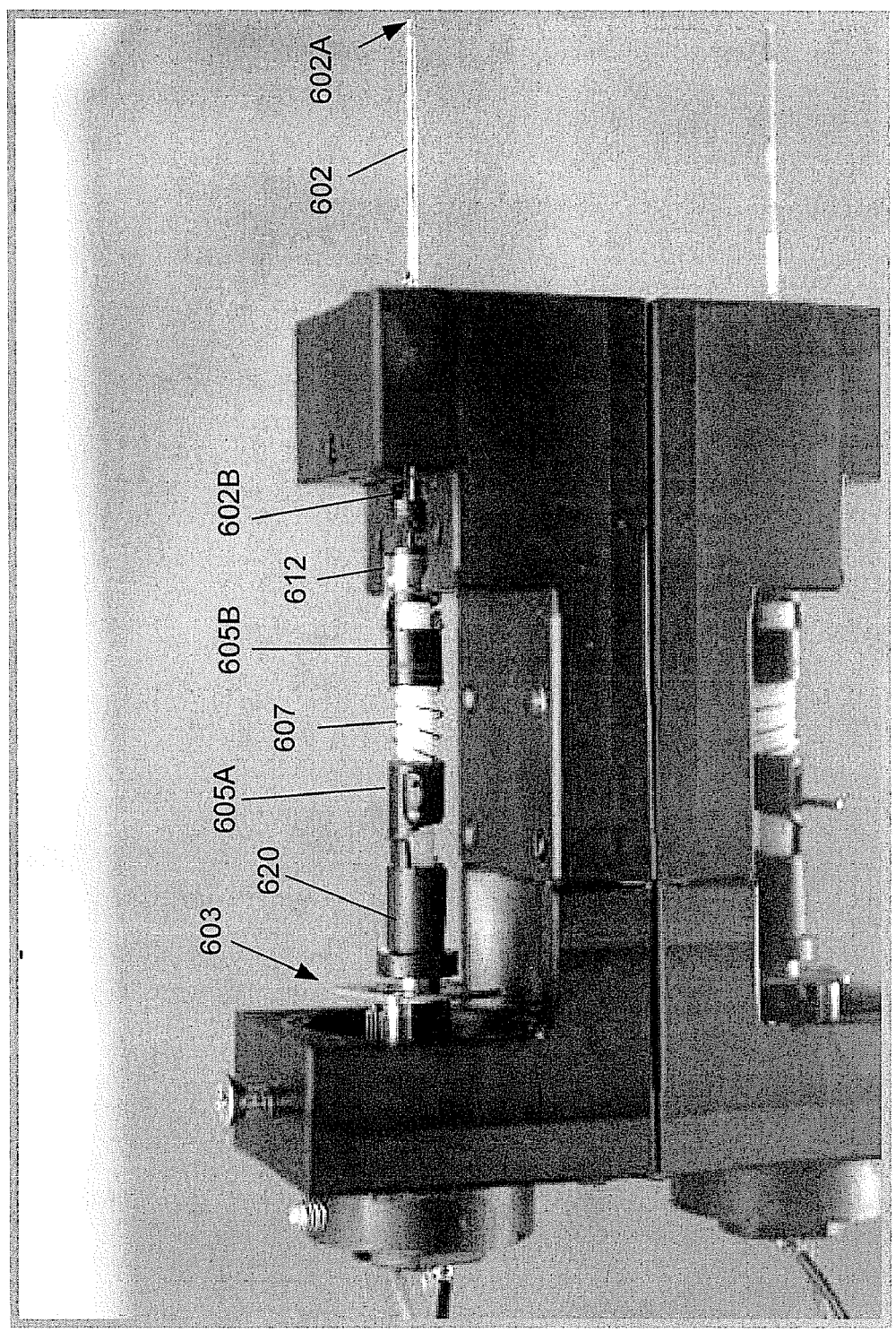
FIG. 6 is a photograph of a working prototype of a cutter (cutting tip) in accordance with an exemplary embodiment of the present disclosure.

FIG. 6 is a photograph of a working prototype of a vitrectomy cutter device 600 in accordance with an exemplary embodiment of the present disclosure. As shown, cutter 600 includes drive housing 612 connected to cutter tip 602, which includes a proximal end 602B (adjacent drive 612) and a distal end 602A. Distal end 602A is useable for cutting vitreous, e.g., as through one or more ports in a housing (e.g., port 306 of FIG. 3). A second drive 620 is located at the opposing end of the prototype and in configured to be driven by a drive 603.

With continued reference to FIG. 6, between drive 612 and 620 is a two-piece locking mechanism having parts 605A and 605B and bias spring 607. Similar to locking mechanism 505 of FIG. 5, the pieces of locking mechanism (605A and 605B) can be positioned at the extremes of longitudinal range along the axis of the cutter 600 to provide one of two different reciprocating cutting motions for cutting tip 602A. For the drive shown, the locking mechanism, 605B, locks with 612 in one direction and lets 620 drive, and in the opposite direction, 605A locks with 620, allowing 612 to drive.

FIG. 7 is a table depicting two exemplary configurations of cutting tips according to the present disclosure. As an example, and not for limitation of the present disclosure, a cutting tip can have a thin horizontal slit 702A, e.g., that is 0.004" wide by 0.0145" deep, may be used for various procedures such as (but not limited to) membrane removal, shaving vitreous base, and operating on a detached retina. In the second configuration, a grater tip 702B is depicted, e.g., perforated with 0.008" diameter holes. This grater can be used, for example, for shaving a retina, working close to a detached retina, and possibly for membrane removal.

FIG. 8 includes FIGS. 8A-8B, which show a cutter 800 operating over different selectable stroke ranges, in accordance with an exemplary embodiment of the present disclosure. As shown in FIG. 8A, cutter 800 includes a cutting tip 802 with a distal end 802A and a proximal end 802B. Inside of the cutting tip is a cutting blade tip 806 that moves in a reciprocating motion over a selectable stroke A. The cutting blade tip 806 can cut tissue introduced through ports 804 and/or 808. The stroke A may be controlled by a cam in a drive mechanism, e.g., as shown and described for FIGS. 4-5. Views (1)-(7) depict the cutter operating over stroke A such that the active port area of the cutter is essentially limited to the holes 808.

With reference to FIG. 8B, the cutter 800 is depicted as operating over a larger selectable stroke B. Views (1)-(9) shown the cutter 806 reciprocating over stroke B. The active port area, in contrast with FIG. 8A, includes not only holes 808 but also major port 804. Such a dual stroke range capability can be provided by a two-cam driver according to the present disclosure, e.g., as shown and described for FIGS. 5A-5E.

It should be understood that in terms of the cut profile, embodiments of the present disclosure can have the ability to move two or more times per revolution on one of the strokes. This would allow the motor to drive in one direction at one speed, and in the other direction at two times the speed. This can be important with a motor drive, because motors have a limited speed range, and embodiments can accordingly double the available speed range of the motor. Exemplary embodiments of the present disclosure have a reduced length stroke that is operated two times per revolution and a large stroke that is operated one time per revolution.

While certain embodiments have been described herein, it will be understood by one skilled in the art that the methods, systems, and apparatus of the present disclosure may be embodied in other specific forms without departing from the spirit thereof.

For example, the tip of the biological tissue cutting handpiece can be modified, e.g., to allow proportional actuation (for a proportional handpiece). Unlike prior art designs, this would be actuated quickly, eliminating the time delay associated with the old versions in the prior art. This is a possible enhancement to the drive mechanism. In exemplary embodiments, forceps could be attached to the tip. The control could be a proportional foot pedal control, or the like.

Accordingly, the embodiments described herein, and as claimed in the attached claims, are to be considered in all respects as illustrative of the present disclosure and not restrictive.

What is claimed:

1. A biological tissue cutting device comprising:
   a cutting tip having one or more ports;
   a cutter within the cutting tip for reciprocating movement across the one or more ports for severing and manipulating tissue drawn into the one or more ports;
   a drive shaft including at least a first and a second groove defining first and second cut profiles, respectively;
   a locking mechanism coupled to the drive shaft such that the locking mechanism does not rotate relative to the drive shaft;
   at least a first and a second drive housing wherein the first drive housing surrounds the first groove and the second drive housing surrounds the second groove, the first and second drive housings further including structure for holding a ball placed within each of the first and second grooves and wherein the cutter is connected to the second drive housing; and wherein when the first drive housing is rotated in a first direction the locking mechanism engages with and prevents rotation of the second drive housing relative to the drive shaft such that the cutter reciprocates according to the first cut profile and when the first drive housing is rotated in an opposite direction the locking mechanism engages with and prevents rotation of the first drive housing relative to the drive shaft such that the cutter reciprocates according to the second cut profile.

2. The biological tissue cutting device of claim 1, wherein the first cut profile and the second cut profile comprise different linear trajectories for a tip of the cutter.

3. The biological tissue cutting device of claim 1, wherein the one or more ports comprise a distal port and a proximal port, wherein the first cut profile cuts at the distal port while the proximal port is occluded by an intermediate portion of the cutter and the second cut profile cuts at the distal and proximal ports.

4. The biological tissue cutting device of claim 1, wherein the one or more ports comprise a plurality of openings having at least two port configurations.

5. The biological tissue cutting device of claim 1, wherein the one or more ports comprise a single slit to allow the cutter to dissect membranes.

6. The biological tissue cutting device of claim 1, wherein the one or more ports comprise a grating structure that has a plurality of small apertures configured and arranged to allow vitreous to enter but prevent retina from entering.

7. The biological tissue cutting device of claim 1, wherein the one or more ports comprise a deep groove configured and arranged for bulk biologic tissue removal.

8. The biological tissue cutting device of claim 1, wherein the one or more ports comprise a rectangular port.

9. The biological tissue cutting device of claim 1, wherein the one or more ports comprise a triangular port that has a vertex aligned toward a distal end of the cutting tip.

10. The biological tissue cutting device of claim 1, wherein the one or more ports comprise a port configured to grip lens fragments, membranes, or clots.

11. The biological tissue cutting device of claim 1, further comprising a motor coupled to the drive shaft.

12. The biological tissue cutting device of claim 11, further comprising a controller for controlling a rotational direction of the motor.

13. The biological tissue cutting device of claim 12, wherein the controller is further configured to control use of the first cut profile and the second cut profile by controlling the rotational direction of the motor.

14. The biological tissue cutting device of claim 12, wherein the controller is further configured to control a cut speed of the cutter by controlling the rotational direction of the motor.

15. A biological tissue cutting device configured and arranged to provide multiple selectable strokes, the device comprising:
a cutting blade tip configured to move in a reciprocating motion;
a cutting tip including one or more ports, the cutting tip configured to receive the cutting blade tip, wherein the one or more ports are configured to provide a variable aperture size based on the position of the cutting blade tip within the cutting tip;
a locking mechanism coupled to a motor, wherein the locking mechanism engages a first drive element when rotated in a first direction, and engages a second drive element when rotated in a second direction; and
wherein the first drive element is configured to reciprocate the cutting blade tip to a first plunge depth within the cutting tip;
wherein the second drive element is configured to reciprocate the cutting blade tip to a second plunge depth within the cutting tip.

16. The biological tissue cutting device of claim 15, wherein the one or more ports comprises a distal port and a proximal port, wherein the first plunge depth cuts at the distal port while the proximal port is occluded by an intermediate portion of the cutter, and the second plunge depth cuts at the distal and proximal ports.

17. The biological tissue cutting device of claim 15, wherein the one or more ports comprise a single slit to allow the cutting blade tip to dissect membranes.

18. The biological tissue cutting device of claim 15, wherein the one or more ports comprise a grating structure that has a plurality of small apertures configured and arranged to allow vitreous to enter but prevent retina from entering.

19. The biological tissue cutting device of claim 15, wherein the one or more ports comprise a deep groove configured and arranged for bulk biologic tissue removal.

* * * * *

UNITED STATES PATENT AND TRADEMARK OFFICE
CERTIFICATE OF CORRECTION

| | | |
|---|---|---|
| PATENT NO. | : 8,172,865 B2 | Page 1 of 1 |
| APPLICATION NO. | : 12/240101 | |
| DATED | : May 8, 2012 | |
| INVENTOR(S) | : Charles DeBoer et al. | |

It is certified that error appears in the above-identified patent and that said Letters Patent is hereby corrected as shown below:

ON THE TITLE PAGE: ITEM (56),

At column 2, line 14, Under Other Publications, after "Opinion" please insert --Received--.

Page 2, at column 2, line 29, Under Other Publications, after "Opinion" please insert --Received--.

Page 2, at column 2, line 31, Under Other Publications, after "Opinion" please insert --Received--.

IN THE SPECIFICATIONS:

At column 4, line 45, please change "lager" to --larger--.

At column 5, line 33, please change "are" to --art--.

Signed and Sealed this
Eleventh Day of September, 2012

David J. Kappos
*Director of the United States Patent and Trademark Office*